United States Patent
Kamei et al.

(10) Patent No.: US 10,450,601 B2
(45) Date of Patent: Oct. 22, 2019

(54) BUFFER COMPOSITION FOR HYBRIDIZATION USE, AND HYBRIDIZATION METHOD

(71) Applicants: Toyo Kohan Co., Ltd., Chiyoda-ku, Tokyo (JP); Yamaguchi University, Yamaguchi-shi, Yamaguchi (JP)

(72) Inventors: Shuichi Kamei, Kudamatsu (JP); Mayuko Hosoya, Kudamatsu (JP); Masaaki Oka, Ube (JP); Shoichi Hazama, Ube (JP); Ryouichi Tsunedomi, Ube (JP)

(73) Assignees: Toyo Kohan Co., Ltd., Tokyo (JP); Yamaguchi University, Yamaguchi-shi, Yamaguchi (JP)

( * ) Notice: Subject to any disclaimer, the term of this patent is extended or adjusted under 35 U.S.C. 154(b) by 0 days.

(21) Appl. No.: 15/024,392

(22) PCT Filed: Sep. 1, 2014

(86) PCT No.: PCT/JP2014/072865
§ 371 (c)(1),
(2) Date: Mar. 24, 2016

(87) PCT Pub. No.: WO2015/045741
PCT Pub. Date: Apr. 2, 2015

(65) Prior Publication Data
US 2016/0265037 A1   Sep. 15, 2016

(30) Foreign Application Priority Data
Sep. 26, 2013  (JP) ................. 2013-200192

(51) Int. Cl.
*C12Q 1/68* (2018.01)
*C07H 21/00* (2006.01)
*C12Q 1/6837* (2018.01)
*C12N 15/09* (2006.01)
*C12Q 1/6816* (2018.01)
*C12Q 1/6832* (2018.01)

(52) U.S. Cl.
CPC ........... *C12Q 1/6837* (2013.01); *C12N 15/09* (2013.01); *C12Q 1/68* (2013.01); *C12Q 1/6816* (2013.01); *C12Q 1/6832* (2013.01)

(58) Field of Classification Search
CPC ....................................................... C12Q 1/68
See application file for complete search history.

(56) References Cited

U.S. PATENT DOCUMENTS

| 5,652,096 A * | 7/1997 | Cimino | C12Q 1/6813 435/6.11 |
| 6,703,228 B1 | 3/2004 | Landers et al. | |
| 7,439,016 B1 | 10/2008 | Anthony et al. | |
| 2001/0014447 A1* | 8/2001 | Milhausen | C07K 14/45 435/6.15 |
| 2001/0029015 A1* | 10/2001 | Ozelius | C07K 14/47 435/6.13 |
| 2002/0015949 A1* | 2/2002 | Erlander | C12Q 1/6809 435/6.16 |
| 2004/0009487 A1* | 1/2004 | Kadushin | C12Q 1/6832 506/4 |
| 2004/0009514 A1* | 1/2004 | Frutos | C07H 21/00 506/9 |
| 2004/0241722 A1* | 12/2004 | Guo | C12Q 1/6876 435/6.11 |
| 2004/0249128 A1* | 12/2004 | Thornton | C07K 14/47 530/350 |
| 2005/0153354 A1* | 7/2005 | Gilmanshin | G01N 33/542 435/6.11 |
| 2005/0250111 A1* | 11/2005 | Xie | C12Q 1/6837 435/6.11 |
| 2006/0229824 A1* | 10/2006 | Cronin | B01J 19/0046 702/19 |
| 2009/0325813 A1* | 12/2009 | Wang | C12Q 1/6837 506/9 |
| 2010/0312582 A1* | 12/2010 | Sorensen | C12Q 1/6883 705/3 |
| 2011/0311974 A1* | 12/2011 | Matthiesen | C12Q 1/6832 435/6.11 |

(Continued)

FOREIGN PATENT DOCUMENTS

| JP | 2002-525127 | 8/2002 |
| JP | 2002-345467 | 12/2002 |
| JP | 2004-511220 | 4/2004 |

(Continued)

OTHER PUBLICATIONS

Cheng et al., Nucleic Acids Research 32 (7) :e61 (2004).*

(Continued)

*Primary Examiner* — Ethan C Whisenant
(74) *Attorney, Agent, or Firm* — McCarter & English, LLP

(57) ABSTRACT

A buffer composition for hybridization of a target nucleic acid is provided. The nucleic acid can include a nucleotide to be detected with a nucleic acid probe. The probe can contain a nucleotide sequence complementary to the target nucleic acid. The buffer can include a blocking nucleic acid having a nucleotide sequence complementary to a non-target nucleic acid having a nucleotide not to be detected corresponding to the nucleotide to be detected. The buffer composition can suppress non-specific hybridization to the nucleic acid probe even when a non-target nucleic acid is present. The use of the buffer composition can achieve excellent detection efficiency of the target nucleic acid.

5 Claims, 6 Drawing Sheets
Specification includes a Sequence Listing.

(56) References Cited

U.S. PATENT DOCUMENTS

2012/0264618 A1* 10/2012 Nygren .............. C12Q 1/6851
 506/2
2014/0377762 A1* 12/2014 Kelly .................. C12Q 1/6858
 435/6.12

FOREIGN PATENT DOCUMENTS

| JP | 2005-502346 | 1/2005 |
| JP | 2007-117060 | 5/2007 |
| JP | 2009-100653 | 5/2009 |
| JP | 2010-200701 | 9/2010 |
| WO | WO03/020902 | 3/2003 |

OTHER PUBLICATIONS

Li et al., Nucleic Acids Research 30 (2) :e5 (2002).*
Iwasaki et al., Accuracy of Genotyping for Single Nucleotide Polymorphisms by a Microarray-Based Single Nucleotide Polymorphism Typing Method Involving Hybridization of Short Allele-Specific Oligonucleotides. DNA Research 9 : 59 (2002). (Year: 2002).*
Parsons et al., Allele-Specific Competitive Blocker—PCR Detection of Rare Base Substitution Methods in Molecular Biology 291 :235 (2005) (Year: 2005).*
Cronin et al., Cystic fibrosi mutation detection by hybridization to light-generated DNA probe arrays. Human Mutation 7 :244 (Year: 1996).*
Hacia et al., Mutational analysis using oligonucleotide microarrays. J. Medical Genetis 36 :730 (Year: 1999).*
Jeffreys et al.,DNA Enrichment by Allele-Specific Hybridization (DEASH): A Novel Method for Haplotyping and for Detecting Low-Frequency Base Substitutional Variants and Recombinant DNA Molecules. Genome Research 13 : 2316 (Year: 2003).*
Zhou et al., Rare allele enrichment and detection by allele-specific PCR, competitive probe blocking, and melting analysis. Biotechniques 50 (5) :311 (Year: 2011).*
International Search Report relating to co-pending International Application No. PCT/JP2014/072865, dated Dec. 2, 2014—1 Page.
Japanese Office Action based on co-pending Japanese Application No. 2015-539042, dated Nov. 13, 2018—7 Pages.

* cited by examiner

SEQUENCE LISTING

<160> NUMBER OF SEQ ID NOS: 20

<210> SEQ ID NO 1
<211> LENGTH: 25
<212> TYPE: DNA
<213> ORGANISM: Artificial
<220> FEATURE:
<223> OTHER INFORMATION: synthetic DNA

<400> SEQUENCE: 1
gtgtgacatg ttctaatata gtcac                                       25

<210> SEQ ID NO 2
<211> LENGTH: 20
<212> TYPE: DNA
<213> ORGANISM: Artificial
<220> FEATURE:
<223> OTHER INFORMATION: synthetic DNA

<400> SEQUENCE: 2
gaatggtcct gcaccagtaa                                             20

<210> SEQ ID NO 3
<211> LENGTH: 16
<212> TYPE: DNA
<213> ORGANISM: Artificial
<220> FEATURE:
<223> OTHER INFORMATION: synthetic DNA

<400> SEQUENCE: 3
gagctggtgg cgtagg                                                 16

<210> SEQ ID NO 4
<211> LENGTH: 18
<212> TYPE: DNA
<213> ORGANISM: Artificial
<220> FEATURE:
<223> OTHER INFORMATION: synthetic DNA

<400> SEQUENCE: 4
ggagctggtg gcgtaggc                                               18

<210> SEQ ID NO 5
<211> LENGTH: 18
<212> TYPE: DNA
<213> ORGANISM: Artificial
<220> FEATURE:
<223> OTHER INFORMATION: synthetic DNA

<400> SEQUENCE: 5
cttggagctg gtggcgta                                               18

<210> SEQ ID NO 6
<211> LENGTH: 18
<212> TYPE: DNA
<213> ORGANISM: Artificial
<220> FEATURE:
<223> OTHER INFORMATION: synthetic DNA

<400> SEQUENCE: 6
gctggtggcg taggcaac                                               18

<210> SEQ ID NO 7
<211> LENGTH: 18
<212> TYPE: DNA
<213> ORGANISM: Artificial

```
<220> FEATURE:
<223> OTHER INFORMATION: synthetic DNA

<400> SEQUENCE: 7
gctggtggcg caggcaac                                                    18

<210> SEQ ID NO 8
<211> LENGTH: 15
<212> TYPE: DNA
<213> ORGANISM: Artificial
<220> FEATURE:
<223> OTHER INFORMATION: synthetic DNA

<400> SEQUENCE: 8
gagctggtgg cgtag                                                       15

<210> SEQ ID NO 9
<211> LENGTH: 19
<212> TYPE: DNA
<213> ORGANISM: Artificial
<220> FEATURE:
<223> OTHER INFORMATION: synthetic DNA

<400> SEQUENCE: 9
tggagctggt ggcgtaggc                                                   19

<210> SEQ ID NO 10
<211> LENGTH: 25
<212> TYPE: DNA
<213> ORGANISM: Artificial
<220> FEATURE:
<223> OTHER INFORMATION: synthetic DNA

<400> SEQUENCE: 10
agttggagct ggtggcgtag gcaag                                            25

<210> SEQ ID NO 11
<211> LENGTH: 15
<212> TYPE: DNA
<213> ORGANISM: Artificial
<220> FEATURE:
<223> OTHER INFORMATION: synthetic DNA

<400> SEQUENCE: 11
gagctggtga cgtag                                                       15

<210> SEQ ID NO 12
<211> LENGTH: 19
<212> TYPE: DNA
<213> ORGANISM: Artificial
<220> FEATURE:
<223> OTHER INFORMATION: synthetic DNA

<400> SEQUENCE: 12
tggagctggt gacgtaggc                                                   19

<210> SEQ ID NO 13
<211> LENGTH: 25
<212> TYPE: DNA
<213> ORGANISM: Artificial
<220> FEATURE:
<223> OTHER INFORMATION: synthetic DNA

<400> SEQUENCE: 13
agttggagct ggtgacgtag gcaag                                            25
```

```
<210> SEQ ID NO 14
<211> LENGTH: 10
<212> TYPE: DNA
<213> ORGANISM: Artificial
<220> FEATURE:
<223> OTHER INFORMATION: synthetic DNA

<400> SEQUENCE: 14
ctggtggcgt                                                          10

<210> SEQ ID NO 15
<211> LENGTH: 15
<212> TYPE: DNA
<213> ORGANISM: Artificial
<220> FEATURE:
<223> OTHER INFORMATION: synthetic DNA

<400> SEQUENCE: 15
gagctggtgg cgtag                                                    15

<210> SEQ ID NO 16
<211> LENGTH: 16
<212> TYPE: DNA
<213> ORGANISM: Artificial
<220> FEATURE:
<223> OTHER INFORMATION: synthetic DNA

<400> SEQUENCE: 16
gagctggtgg cgtagg                                                   16

<210> SEQ ID NO 17
<211> LENGTH: 18
<212> TYPE: DNA
<213> ORGANISM: Artificial
<220> FEATURE:
<223> OTHER INFORMATION: synthetic DNA

<400> SEQUENCE: 17
ggagctggtg gcgtaggc                                                 18

<210> SEQ ID NO 18
<211> LENGTH: 19
<212> TYPE: DNA
<213> ORGANISM: Artificial
<220> FEATURE:
<223> OTHER INFORMATION: synthetic DNA

<400> SEQUENCE: 18
tggagctggt ggcgtaggc                                                19

<210> SEQ ID NO 19
<211> LENGTH: 25
<212> TYPE: DNA
<213> ORGANISM: Artificial
<220> FEATURE:
<223> OTHER INFORMATION: synthetic DNA

<400> SEQUENCE: 19
agttggagct ggtggcgtag gcaag                                         25

<210> SEQ ID NO 20
<211> LENGTH: 30
```

```
<212> TYPE: DNA
<213> ORGANISM: Artificial
<220> FEATURE:
<223> OTHER INFORMATION: synthetic DNA

<400> SEQUENCE: 20
gtagttggag ctggtggcgt aggcaagagt                                        30
```

BUFFER COMPOSITION FOR HYBRIDIZATION USE, AND HYBRIDIZATION METHOD

RELATED APPLICATION

This application is a national stage application filed under 35 USC 371 of PCT/JP2014/072865, filed Sep. 1, 2014, which claims the benefit of Japanese Patent Application No. 2013-200192, filed Sep. 26, 2013, all of which are incorporated herein, in entirety, by reference.

Submission Of Sequence Listing

The Sequence Listing associated with this application is filed in electronic format via EFS-Web and hereby incorporated by reference into the specification in its entirety. The name of the text file containing the Sequence Listing is 119244_00092_Sequence_Listing. The size of the text file is 4 KB, and the text file was created on Mar. 22, 2016.

TECHNICAL FIELD

The present invention relates to a buffer composition for hybridization, used for hybridization of a target nucleic acid comprising a nucleotide to be detected with a nucleic acid probe comprising a nucleotide sequence complementary to the target nucleic acid, and a hybridization method.

BACKGROUND ART

For example, in molecular biology, hybridization means a phenomenon in which nucleic acids hydrogen-bond to each other through complementary base pairing. In other words, if the nucleotide sequence of a nucleic acid molecule to be measured is known, a nucleic acid molecule having a nucleotide sequence complementary to the nucleotide sequence can be used to detect the nucleic acid molecule to be measured. More specifically, this is a method which involves reacting a fluorescence-labeled nucleic acid to be measured with a solid phase on which a nucleic acid probe having a nucleotide sequence complementary to the nucleic acid molecule to be measured is immobilized, washing/removing the unreacted nucleic acid molecules, and measuring the activity of the labeled substance bound to the solid phase. The hybridization method can detect a nucleic acid molecule to be measured by accurately recognizing the DNA sequence.

To accurately detect a nucleic acid molecule to be measured in the hybridization, it is important for a nucleic acid probe to accurately recognize the nucleic acid molecule. Hence, in conducting hybridization, a method involving properly regulating the salt concentration and reaction temperature of a reaction solution or a method involving using a blocking agent for suppressing non-specific hybridization of a nucleic acid probe with nucleic acid molecules other than that to be measured have conventionally been used. Known examples of the blocking agent include nucleic acid components not having nucleotide sequences complementary to a nucleic acid molecule to be measured and a nucleic acid probe, such as salmon sperm DNA and yeast tRNA, surfactants, such as SDS (sodium dodecyl sulfate) and N-lauroyl sarcosine (N-LS), and proteins, such as bovine serum albumin (BSA) and casein.

However, when nucleic acid molecules not to be measured are abundantly present, there are problems that the blocking agents consisting of nucleic acid components exhibit insufficient blocking effects and the surfactants and the proteins have weak blocking effects because they cannot exactly recognize nucleotide sequences.

Patent Literature 1 discloses a method which involves using a blocker probe hybridizing with a unique sequence in a nucleic acid molecule to be measured and specifically hybridizing with a capture sequence probe containing a nucleic acid sequence captured on a solid phase. In the method described in Patent Literature 1, the blocker probe is added to a reaction solution after the hybridization of the capture sequence probe to the nucleic acid molecule to be measured to prevent the unhybridized capture sequence probe from hybridizing with a crossreactive nucleic acid sequence present in the nucleic acid molecule to be measured, thereby enabling the enhancement of detection specificity.

In addition, Patent Literature 2 discloses the use of an oligonucleotide containing a modified nucleotide, such as a locked nucleic acid (LNA), as a blocking agent when a nucleic acid molecule to be measured is detected using a microarray.

Furthermore, Patent Literature 3 discloses a method which involves detecting a nucleic acid molecule to be measured with a nucleic acid probe using a 5'-terminal block nucleic acid hybridizing with 5'-end side to a nucleotide to be detected in a nucleic acid molecule to be measured and a 3'-terminal block nucleic acid hybridizing with 3'-end side to the nucleotide to be detected. The method in Patent Literature 3 is considered to have a high nucleotide sequence specificity in hybridization of the probe nucleic acid with the target nucleic acid, enabling the enhancement of the efficiency and specificity of the typing of SNP required to detect the difference of only one nucleotide in a nucleotide sequence with high accuracy and the detection and separation of a nucleic acid having a particular nucleotide sequence.

CITATION LIST

Patent Literature

Patent Literature 1
  JP Patent Publication (Kohyo) No. 2004-511220 A
Patent Literature 2
  JP Patent Publication (Kohyo) No. 2005-502346 A
Patent Literature 3
  JP Patent Publication (Kokai) No. 2010-200701 A

SUMMARY OF INVENTION

Technical Problem

However, when a target nucleic acid comprising a nucleotide to be detected is detected with a nucleic acid probe, there is a problem that the presence of a non-target nucleic acid comprising a nucleotide not to be detected corresponding to the nucleotide to be detected decreases the efficiency of hybridization of the target nucleic acid with the nucleic acid probe and decreases the efficiency of the detection of the target nucleic acid. Accordingly, in view of the above circumstances, an object of the present invention is to suppress non-specific hybridization to the nucleic acid probe even when the non-target nucleic acid is present to achieve the excellent detection efficiency of the target nucleic acid.

Solution to Problem

After diligent study to achieve the above-mentioned object, the present inventors have succeeded in designing a blocking nucleic acid capable of enhancing detection efficiency in detecting a target nucleic acid using a probe nucleic acid, thereby accomplishing the present invention. The present invention encompasses the following.

(1) A buffer composition for hybridization used for hybridization of a target nucleic acid comprising a nucleotide to be detected with a nucleic acid probe comprising a nucleotide sequence complementary to the target nucleic acid, comprising a blocking nucleic acid comprising a nucleotide sequence complementary to a non-target nucleic acid comprising a nucleotide not to be detected corresponding to the nucleotide to be detected.

(2) The buffer composition for hybridization according to (1), wherein the blocking nucleic acid has a length of 60% or more of the nucleotide length of the nucleic acid probe.

(3) The buffer composition for hybridization according to (1), wherein the blocking nucleic acid has a length shorter than the nucleotide length of the nucleic acid probe.

(4) The buffer composition for hybridization according to (1), wherein the nucleic acid probe is 15 to 25 bases in length and the blocking nucleic acid is 15 to 24 bases in length.

(5) The buffer composition for hybridization according to (1), wherein the buffer composition is used in a microarray in which the nucleic acid probe is immobilized on a substrate.

(6) The buffer composition for hybridization according to (1), further comprising sodium citrate dihydrate (SSC) and sodium dodecyl sulfate (SDS).

(7) The buffer composition for hybridization according to (1), wherein the buffer composition is mixed with a reaction solution after nucleic acid amplification reaction for amplifying the target nucleic acid.

(8) A method for hybridization of a target nucleic acid comprising a nucleotide to be detected with a nucleic acid probe comprising a nucleotide sequence complementary to the target nucleic acid, comprising: mixing a buffer composition for hybridization comprising a blocking nucleic acid comprising a nucleotide sequence complementary to a non-target nucleic acid comprising a nucleotide not to be detected corresponding to the nucleotide to be detected with a solution comprising the target nucleic acid; and then hybridizing the nucleic acid probe with the target nucleic acid.

(9) The hybridization method according to (8), wherein the blocking nucleic acid has a length of 60% or more of the nucleotide length of the nucleic acid probe.

(10) The hybridization method according to (8), wherein the blocking nucleic acid has a length shorter than the nucleotide length of the nucleic acid probe.

(11) The hybridization method according to (8), wherein the nucleic acid probe is 15 to 25 bases in length and the blocking nucleic acid is 15 to 24 bases in length.

(12) The hybridization method according to (8), wherein a mixed solution of the buffer composition for hybridization and the solution comprising the target nucleic acid is contacted with a microarray in which the nucleic acid probe is immobilized on a substrate.

(13) The hybridization method according to (8), wherein the buffer composition for hybridization further comprises sodium citrate dihydrate (SSC) and sodium dodecyl sulfate (SDS).

(14) The hybridization method according to (8), wherein the solution comprising the target nucleic acid is a reaction solution after nucleic acid amplification reaction for amplifying the target nucleic acid and the reaction solution is mixed with the buffer composition for hybridization.

The present specification encompasses the contents of the specification and/or drawings of Japanese Patent Application No. 2013-200192 on which the priority of the present application is based.

Advantageous Effects of Invention

According to the buffer composition for hybridization and the hybridization method according to the present invention, the non-specific hybridization can be suppressed between a nucleic acid molecule other than a target nucleic acid comprising a nucleotide to be detected and a probe nucleic acid. Thus, the buffer composition for hybridization and the hybridization method according to the present invention can be applied to considerably enhance the efficiency of the detection of the target nucleic acid based on specific hybridization of the target nucleic acid with the probe nucleic acid.

DESCRIPTION OF EMBODIMENTS

Figure 1:
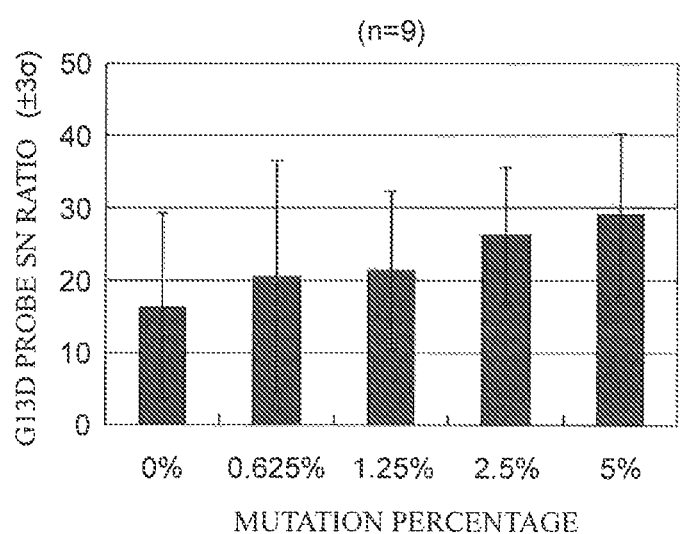
FIG. 1 is a characteristic graph showing the results of calculating G13D detection probe fluorescence intensity/BG (S/N ratio) when a buffer composition for hybridization containing no blocking nucleic acid was used.

The buffer composition for hybridization according to the present invention is a buffer composition used for hybridization of a target nucleic acid comprising a nucleotide to be detected with a nucleic acid probe comprising a nucleotide sequence complementary to the target nucleic acid. Particularly, the buffer composition for hybridization according to the present invention comprises a blocking nucleic acid having the function of suppressing non-specific hybridization to the nucleic acid probe.

As used herein, the target nucleic acid means a nucleic acid molecule, i.e., a nucleic acid fragment, comprising a nucleotide to be detected. The target nucleic acid may be a nucleic acid molecule consisting of DNA, a nucleic acid molecule consisting of RNA, or a nucleic acid molecule containing DNA and RNA (DNA-RNA complex). The nucleic acid is meant to include adenine, cytosine, guanine, thymine, and uracil and artificial nucleic acids, such as a peptide nucleic acid (PNA) and a locked nucleic acid (INA).

The nucleotide to be detected means, for example, one or a plurality of nucleic acid residues at a predetermined position in a chromosome or, is not particularly limited: the type of a particular nucleotide in a nucleotide sequence, such as a single nucleotide polymorphism (SNP). For example, when a predetermined single nucleotide polymorphism is assumed to be capable of taking A (adenine) or C (cytosine), either nucleotide, i.e., A (adenine) in the single nucleotide polymorphism, may be a nucleotide to be detected. Here, the nucleotide to be detected may be the major allele or the minor allele in a gene polymorphism, and may be a risk allele or not.

The target nucleic acid comprising a nucleotide to be detected can be prepared by amplifying a predetermined region comprising the nucleotide to be detected by a nucleic acid amplification method. The target nucleic acid may be cDNA obtained by reverse transcription reaction from a transcriptional product collected from individual organisms, tissue, or cells. The nucleotide length of the target nucleic acid is not particularly limited; however, it may be, for example, 60 to 1,000 bases, preferably 60 to 500 bases, more preferably 60 to 200 bases.

Against the target nucleic acid comprising a nucleotide to be detected, the nucleic acid molecule (nucleic acid fragment) comprising a nucleotide not to be detected corresponding to the nucleotide to be detected is referred to as a non-target nucleic acid. For example, when of a plurality of nucleotides capable of being taken at a predetermined position in a chromosome. one nucleotide is a nucleotide to be detected, a nucleotide other than the nucleotide to be detected is defined as a nucleotide not to be detected. More specifically, when a single nucleotide polymorphism at a predetermined position can take A (adenine) or C (cytosine). it follows that if A (adenine) in the single nucleotide polymorphism is a nucleotide to be detected, C (cytosine) in the single nucleotide polymorphism is a nucleotide not to be detected.

When a nucleotide not to be detected is present in a chromosome, a non-target nucleic acid comprising g the nucleotide not to be detected is simultaneously obtained in obtaining a target nucleic acid comprising a nucleotide to be detected as described above. For example, when the target nucleic acid is obtained by a nucleic acid amplification reaction, such as polymerase chain reaction, it follows that if one allele is a nucleotide not to be detected, a non-target nucleic acid is amplified together with the target nucleic acid.

To detect a target nucleic acid comprising a nucleotide to be detected, a nucleic acid probe is used which has a nucleotide sequence complementary to a region at least comprising the nucleotide to be detected in the target nucleic acid. The nucleic acid probe is not particularly limited; however, it is, for example, 10 to 30 bases in length, preferably 15 to 25 bases in length. When the nucleotides constituting the nucleic acid probe are viewed as a string of letter, the nucleotide complementary to the nucleotide to be detected is preferably at a position representing the center of the string. The center of the string is meant to include a case where for a nucleic acid probe consisting of an even number of nucleotides, one nucleotide is off-centered toward the 5'-end or 3'-end thereof.

In the buffer composition for hybridization according to the present invention, the blocking nucleic acid has a nucleotide sequence complementary to a region comprising a nucleotide not to be detected in a non-target nucleic acid. Hence, the blocking nucleic acid can hybridize with the non-target nucleic acid under conditions enabling hybridization of the target nucleic acid with the nucleic acid probe. The blocking nucleic acid is not particularly limited; however, it preferably has a length of 60% or more of the nucleotide length of the nucleic acid probe. The blocking nucleic acid also preferably has a length shorter than the nucleotide length of the nucleic acid probe. For example, when the nucleic acid probe is assumed to be 25 bases in length, the blocking nucleic acid is preferably 15 to 24 bases in length.

In the blocking nucleic acid, when the nucleotides constituting the blocking nucleic acid are viewed as a string of letters, the nucleotide complementary to the nucleotide not to be detected is preferably at a position representing the center of the string. The center of the string is meant to include a case where for a blocking nucleic acid consisting of an even number of nucleotides, one nucleotide is off-centered toward the 5'-end or 3'-end thereof.

In addition, the blocking nucleic acid may comprise a mismatch nucleotide (a non-complementary nucleotide) at a position corresponding to a nucleotide other than the nucleotide not to be detected contained in the non-target nucleic acid. When the blocking nucleic acid is 15 bases in length, the number of the mismatch nucleotides may be 1 to 3, preferably 1 to 2. When the blocking nucleic acid is 24 bases in length, the number of the mismatch nucleotides may be 1 to 3, preferably 1 to 2.

Furthermore, in the buffer composition for hybridization according to the present invention, the concentration of the blocking nucleic acid is not particularly limited; however, for example, it may be properly set depending on the concentration of the non-target nucleic acid and/or the concentration of the target nucleic acid or depending on the primer concentration. Specifically, the concentration of the blocking nucleic acid in the composition may be 0.01 to 1 µM, preferably 0.05 to 0.75 µM, more preferably 0.125 to 0.5 µM.

As described above, the buffer composition for hybridization according to the present invention can suppress non-specific hybridization of a non-target nucleic acid with a nucleic acid probe because of comprising a blocking nucleic acid and can prevent the inhibition of specific hybridization of a target nucleic acid with the nucleic acid probe. As such, the use of the buffer composition for hybridization according to the present invention enables the detection of a target nucleic acid with high accuracy using a nucleic acid probe, for example, even when the concentration of the target nucleic acid is low. The use of the buffer composition for hybridization according to the present invention also enables the detection of a target nucleic acid with high accuracy using a nucleic acid probe, for example, even when a non-target nucleic acid different in only one nucleotide from the target nucleic acid is present.

The buffer composition for hybridization according to the present invention can be used in any system involving hybridization meaning complementary binding between nucleic acid molecules. Specifically, the buffer composition for hybridization according to the present invention can be used in Southern hybridization, Northern hybridization, and in situ hybridization. Particularly, the buffer composition for hybridization according to the present invention is preferably used in a system in which a nucleic acid probe is immobilized on a support (including a substrate, a hollow fiber, and a fine particle) to perform the detection (including qualification and quantification) of a target nucleic acid using the immobilized nucleic acid probe. More specifically, the buffer composition for hybridization according to the present invention is most preferably used in detecting a target nucleic acid using a DNA microarray (DNA chip) in which a nucleic acid probe is immobilized on a substrate.

A system is illustratively described below in which the buffer composition for hybridization according to the present invention is used in detecting a target nucleic acid using a DNA microarray (DNA chip). The embodiment of the buffer composition for hybridization according to the present invention is not intended to be limited to the following example.

The example is a target nucleic acid to be measured in which a wild-type sequence, GGTGGC, is contained with respect to the 12th codon (codon 12) and the 13th codon (codon 13) in K-ras (v-Ki-ras2 Kirsten rat sarcoma viral oncogene homolog). Hence, the nucleic acid comprising a sequence in which one of codon 12 and codon 13 is of mutant type is a non-target nucleic acid. For codon 12, G12C, G12A, G12D, G12R, G12S, and G12V mutations are known. For codon 13, G13C, G13A, G13D, G13R, G13S, and G13V mutations are known.

When a plurality of non-target nucleic acids are present, blocking nucleic acids may be provided for all the non-target nucleic acids, or blocking nucleic acids may be provided for some non-target nucleic acids.

The nucleic acid probe and the blocking nucleic acid are each more preferably a single-stranded DNA. The nucleic acid probe and the blocking nucleic acid can be obtained, for example, by chemical synthesis using a nucleic acid synthesis device. As the nucleic acid synthesis device, devices called a DNA synthesizer, a fully automatic nucleic acid synthesizer. or an automated nucleic acid synthesizer can be used.

In this example, the nucleic acid probe is preferably used in the form of a microarray by immobilizing the 5'-end thereof on a support. The material of the support may be one well-known in the art and is not particularly limited. Examples thereof include noble metals, such as platinum, platinum black, gold, palladium, rhodium, silver, mercury, tungsten, and their compounds, and electric conductor materials, such as carbons typified by graphite and carbon fiber; silicon materials typified by single crystal silicon, amorphous silicon, silicon carbide, silicon oxide, and silicon nitride, and composite materials composed of silicon materials, typified by SOI (silicon-on-insulator) and the like; inorganic materials, such as glass, quartz glass, alumina, sapphire, ceramics, forsterite, and photosensitive glass; and organic materials. such as polyethylene, ethylene, polypropylene, cyclic polyolefins, polyisobutylene. polyethylene terephthalate, unsaturated polyesters, fluorine-containing resins, polyvinyl chloride, polyvinylidene chloride, polyvinyl acetate, polyvinyl alcohols, polyvinyl acetal, acrylic resin, polyacrylonitrile, polystyrene, acetal resin, polycarbonate, polyamides, phenol resin, urea resin, epoxy resin, melamine resin, styrene-acrylonitrile copolymer, acrylonitrile-butadiene-styrene copolymer, polyphenylene oxide, and polysulfone. The shape of the support is also not particularly limited; however, it is preferably tabular.

As the support, a support is preferably used which has a carbon layer, such as diamond-like carbon (DLC), and chemically modifying groups, such as an amino group, a carboxyl group, an epoxy group, a formyl group, a hydroxyl group, and an active ester group, on the surface. Supports having a carbon layer and chemically modifying groups on the surface include one having a carbon layer and chemically modifying groups on the surface of a substrate and one having chemically modifying groups on the surface of a substrate composed of a carbon layer. The material for the substrate may be one well-known in the art, is not particularly limited, and may be the same one as any of those exemplified as the above support materials.

A target nucleic acid in a subject can be detected using the DNA microarray thus prepared. The detection comprises a step of extracting DNA from a sample derived from the subject, a step of using the extracted DNA as a template to amplify a region containing codons 12 and 13 in K-ras, and a step of detecting the amplified nucleic acid using a DNA microarray.

The subject is typically a human, and examples thereof include patients suffering from large bowel cancer including colonic cancer and rectal cancer, head and neck cancer, or non-small cell lung cancer. The subject may be a healthy individual not suffering from these cancers. In addition, the subject may also be a patient suffering from EGFR-positive, advanced/recurrent colonic/rectal cancer. The sample derived from a subject is not particularly limited. Examples thereof include blood-related samples (e.g., blood, serum, and plasma), lymph fluid, stool, and the debris and extract of cancer cells, tissue, or organ.

First, DNA is extracted from a sample collected from a patient. The means for extraction is not particularly limited. For example, a DNA extraction method can be used which uses phenol/chloroform, ethanol, sodium hydroxide, CTAB, or the like.

Then, amplification reaction is conducted using the resultant DNA as a template to amplify a nucleic acid, preferably DNA, encoding K-RAS gene. As the amplification reaction, a method, such as polymerase chain reaction (PCR), LAMP (loop-mediated isothermal amplification), or ICAN (isothermal and chimeric primer-initiated amplification of nucleic acids), can be applied. For the amplification reaction, it is desirable to add a label so that the amplified region can be identified. At this time, the method for labeling the amplified nucleic acid is not particularly limited; however, it may be, for example, a method which involves labeling primers used for amplification reaction in advance, or a method which involves using a labeled nucleotide as a substrate for amplification reaction. The labeling substance is not particularly limited; however, it may be a radioactive isotope, a fluorescent dye, or an organic compound, such as digoxigenin (DIG) or biotin.

The reaction system is a reaction system containing a buffering agent necessary for the amplification/labeling of a nucleic acid, a thermostable DNA polymerase, primers specific for K-RAS gene. a labeled nucleotide triphosphate (specifically, a nucleotide triphosphate to which a fluorescent label or the like is added), a nucleotide triphosphate, magnesium chloride, and the like.

The primer used for the amplification reaction is not particularly limited provided that it can specifically amplify a region containing codon 12 and codon 13 in K-ras, and can be properly designed by those of ordinary skill in the art. Examples thereof include a primer set consisting of:

```
primer 1:
                                  (SEQ ID NO: 1)
5'-gtgtgacatgttctaatatagtcac-3',
and, primer 2:
                                  (SEQ ID NO: 2)
5'-gaatggtcctgcaccagtaa-3'.
```

The amplified nucleic acids as described above include a target nucleic acid and a non-target nucleic acid. The hybridization reaction between a nucleic acid probe and the target nucleic acid can be conducted to measure the amount of the nucleic acid hybridized with the nucleic acid probe, for example, by detecting a label. The intensity of a signal from the label can be digitalized, for example, by detecting a fluorescent signal on a fluorescence scanner when a fluorescent label is used and analyzing it using an image analysis software. The amplified nucleic acid hybridized with the nucleic acid probe can also be quantified, for example, by preparing a calibration curve using a sample containing a known amount of DNA.

At this time, the above-described buffer composition for hybridization according to the present invention can be used to suppress non-specific hybridization of the non-target nucleic acid with the nucleic acid probe. The hybridization reaction using the buffer composition for hybridization is preferably conducted under stringent conditions. The stringent conditions refer to conditions under which a specific hybrid is formed without the formation of any non-specific hybrid, refer to conditions of hybridization reaction at 50° C. for 16 hours, followed by washing under conditions of 2×SSC/0.2% SDS at 25° C. for 10 minutes and 2×SSC at 25° C. for 5 minutes. In other words, the buffer composition for hybridization according to the present invention may contain a salt necessary for hybridization reaction, e.g., SSC, and a well-known blocking agent, e.g., SDS.

A reaction solution containing the target nucleic acid and the non-target nucleic acid after amplification reaction may be mixed with the buffer composition for hybridization according to the present invention to make specific hybridization of the non-target nucleic acid with a blocking nucleic acid, followed by contacting the reaction solution with a DNA microarray to allow hybridization reaction between the target nucleic acid and the nucleic acid probe to proceed. Alternatively, the reaction solution containing the target nucleic acid and the non-target nucleic acid after amplification reaction may be mixed with the buffer composition for hybridization according to the present invention on a DNA microarray to allow specific hybridization of the non-target nucleic acid with the blocking nucleic acid to proceed simultaneously with specific hybridization of the target nucleic acid with the nucleic acid probe.

EXAMPLES

The present invention will be described below in further detail with reference to Examples. However, the following Examples are not intended to limit the technical scope of the present invention.

Example 1

In this Example, the wild-type nucleotide sequence (GGTGGC) of codons 12 and 13 in K-ras was used as a nucleotide not to be detected. As a wild-type specimen, the genomic DNA of the strain RKO (the sequence of codons 12 and 13 in the wild-type specimen: GGTGGC) was used. As a nucleotide to be detected, the genomic DNA of the strain LoVo (G13D mutant specimen, the sequence of codons 12 and 13: GGTGAC) was used. DNAs extracted from these cell lines were used to prepare 5 specimen DNAs in each of which the percentage of the G13D mutant specimen was 0%, 0.625%, 1.25%, 2.5% or 5%.

Using each of these 5 specimen DNAs, PCR was performed under the conditions of Tables 1 and 2.

TABLE 1

| Temperature | Time | Cycle |
|---|---|---|
| 95° C. | 5 min | |
| 95° C. | 30 sec | |
| 55° C. | 30 sec | 40 cycles |
| 72° C. | 30 sec | |
| 72° C. | 5 min | |

TABLE 2

| Reagent | Maker | Concentration of Stock Solution | Liquid Volume (μL) |
|---|---|---|---|
| 10× Buffer | Roche | 10× | 5 |
| dNTP | Roche | 10 mM | 1 |
| FW | Sigma Genosys | 100 μM | 0.1 |
| RV (Fluorescent Label) | Sigma Genosys | 60.5 μM | 0.33 |
| Specimen DNA | | 5 ng/μL | 6 |
| tap Polymerase | Roche | 5 U/μL | 0.4 |
| MiliiQ | | | 37.17 |
| total | | | 50 |

A buffer composition for hybridization containing a blocking nucleic acid (sequence: GAGCTGGTGGCG-TAGG (SEQ ID NO: 3)) (3×SSC/0.3% SDS/blocking nucleic acid/0.4 nM Cy5 oligo DNA) or a buffer composition for hybridization containing no blocking nucleic acid (3×SSC/0.3% SDS/0.4 nM Cy5 oligo DNA) was mixed with the resultant PCR products at a ratio of 1:2 to make a hybridization reaction solution.

The hybridization reaction solution was stepwise added to a DNA chip, covered with a hybridization cover, and reacted at 54° C. for 1 hour using a hybridization chamber. As the DNA chip, Gene Silicon (R) (from Toyo Kohan Co. Ltd.) was used.

After the end of reaction, the solution was washed with 1×SSC/0.1% SDS for 5 minutes (vertically shaken 30 times and then allowed to stand) and with 1×SSC for 3 minutes (vertically shaken 30 times and then allowed to stand). Then, the resultant was covered with a cover film and measured for fluorescence intensity using Bioshot. And, G13D detection probe fluorescence intensityBG (S/N ratio) was calculated based on the resultant fluorescence intensity.

Figure 2:
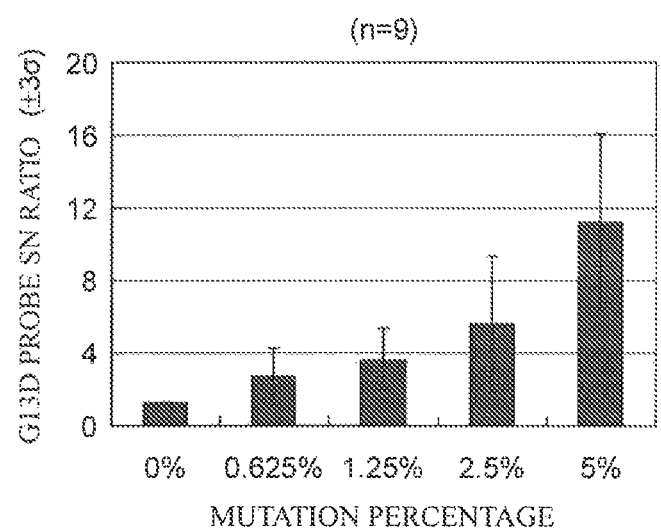
FIG. 2 is a characteristic graph showing the results of calculating G13D detection probe fluorescence intensity/BG (S/N ratio) when a buffer composition for hybridization containing a blocking nucleic acid was used.

The calculation results are shown in FIGS. 1 and 2. FIG. 1 shows the results when the buffer composition for hybridization containing no blocking nucleic acid was used, and FIG. 2 shows the results when the buffer composition for hybridization containing the blocking nucleic acid was used. FIGS. 1 and 2 show the average S/N ratios in a wt probe and a G13D probe for 5 specimen DNAs.

As shown in FIG. 2, when the blocking nucleic acid is contained. the S/N ratio in the G13D probe was 1.2 for a G13D mutant specimen percentage of 0% and non-specific reaction was almost suppressed. As shown in FIG. 1, when the blocking nucleic acid is not contained, non-specific hybridization to the G13D probe was observed even for a G13D mutant specimen percentage of 0%.

FIG. 2 also shows that the G13D mutant specimen percentage of 0.625% or more tends to increase the SN ratio percentage-dependently. However, as shown in FIG. 1, when the blocking nucleic acid is not contained, variation in the SN ratio for the G13D probe is increased irrespective of the percentage of the G13D mutant specimen. In contrast, FIG. 2 shows that when the blocking nucleic acid is contained, variation in the SN ratio for the G13D probe is decreased.

In addition, it was shown that whereas the detection sensitivity was positive for on the order of 5% when the blocking nucleic acid was not contained (FIG. 1), detection was possible even for on the order of 0.625% when the blocking nucleic acid was contained (FIG. 2).

From the above results, it is probable that hybridization of the target nucleic acid with the nucleic acid probe was conducted in the presence of the blocking nucleic acid to suppress non-specific reaction and decrease variation to stabilize a signal and enhance detection sensitivity.

Example 2

In this Example, the position of a nucleotide sequence complementary to a nucleotide not to be detected and the mismatch nucleotide contained in a blocking nucleic acid were studied.

In this Example, PCR (Tables 1 and 2) was performed in the same way as in Example 1 except for using, as a wild-type specimen, the genomic DNA of the strain SW948 (the sequence of codons 12 and 13 in the wild-type specimen: GGTGGC). In this example, the genomic DNA of the strain SW948 and the genomic DNA of the strain LoVo were independently subjected to PCR without being mixed.

In this example, each PCR product, a buffer solution (3×SSC/0.3% SDS/0.4 nM Cy5 oligo DNA), and a blocking nucleic acid (concentration: 0.125 μM, 0.25 μM, or 0.5 μM) were mixed at a ratio of 1:1:1 to make a hybridization reaction solution. The nucleotide sequence of the blocking nucleic acid used is shown in Table 3. Purified water was used as a control which contains no blocking nucleic acid.

TABLE 3

| Blocker | Sequence (5'→3') | Number of Mismatches | SEQ ID NO: |
|---|---|---|---|
| KP-18 | GGAGCTGGTGGCGTAGGC | 0 | 4 |
| KP-18R | CTTGGAGCTGGTGGCGTA | 0 | 5 |
| KP-18L | GCTGGTGGCGTAGGCAAC | 0 | 6 |
| KR-18-1 | GCTGGTGGCGC̲AGGCAAC | 1 | 7 |

*Bold letters: the sequence of codons 12 and 13, underline: mismatch sequence.

The resultant hybridization reaction solution was stepwise added to a DNA chip. covered with a hybridization cover, and reacted at 54° C. for 1 hour using a hybridization chamber. As the DNA chip, the same one as that used in Example 1 was used.

After the end of reaction, the solution was washed with 1×SSC/0.1% SDS for 5 minutes (vertically shaken 30 times and then allowed to stand) and with 1×SSC for 3 minutes (vertically shaken 30 times and then allowed to stand). Then, the resultant was covered with a cover film and measured for fluorescence intensity using Bioshot. And, G13D detection probe fluorescence intensity/BG (S/N ratio) was calculated based on the resultant fluorescence intensity.

Figure 3:
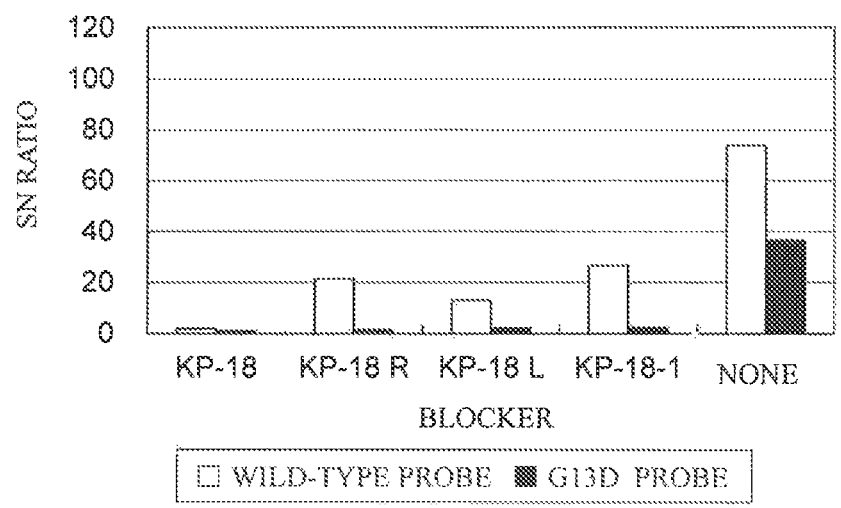
FIG. 3 is a characteristic graph showing the S/N ratios of a wt probe and a G13D probe when each blocking nucleic acid was used for PCR products prepared using wild-type genomic DNA.
Figure 4:
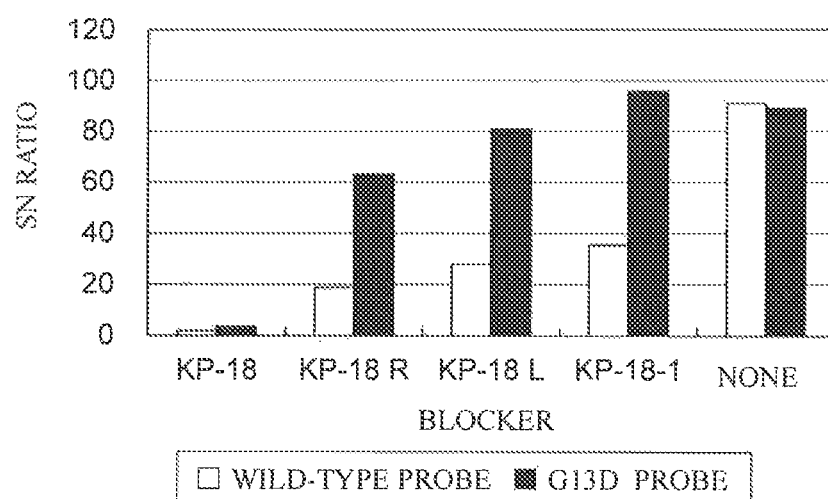
FIG. 4 is a characteristic graph showing the S/N ratios of a wt probe and a G13D probe when each blocking nucleic acid was used for PCR products prepared using mutant genomic DNA.

The calculation results are shown in Tables 4 and 5 and FIGS. 3 and 4. Table 4 and FIG. 3 show the SN ratios in a wt probe and a G13D probe when each blocking nucleic acid was used for the PCR product prepared using the wild-type genomic DNA. Table 5 and FIG. 4 show the SN ratios in a wt probe and a G13D probe when each blocking nucleic acid was used for the PCR product prepared using the mutant genomic DNA.

TABLE 4

| Blocker | KP-18 | KP-18 | KP-18 | KP-18R | KP-18L | KP-18-1 | None |
|---|---|---|---|---|---|---|---|
| Concentration | 0.125 | 0.25 | 0.5 | 0.5 | 0.5 | 0.5 | — |
| Wild-type | 6.58 | 2.41 | 1.90 | 21.37 | 13.08 | 26.73 | 73.78 |
| G13D | 3.75 | 1.98 | 1.07 | 1.62 | 1.63 | 2.56 | 36.79 |

TABLE 5

| Blocker | KP-18 | KP-18 | KP-18 | KP-18R | KP-18L | KP-18-1 | None |
|---|---|---|---|---|---|---|---|
| Concentration | 0.125 | 0.25 | 0.5 | 0.5 | 0.5 | 0.5 | — |
| Wild-type | 1.05 | 1.00 | 1.89 | 18.77 | 27.79 | 35.44 | 91.08 |
| G13D | 8.94 | 4.26 | 3.65 | 63.17 | 80.95 | 95.64 | 89.2 |
| G13D/Wild-type | 8.49 | 4.25 | 1.93 | 3.37 | 2.91 | 2.70 | 0.98 |

Tables 4 and 5 and FIGS. 3 and 4 showed that the blocking nucleic acid having a nucleotide sequence complementary to the nucleotide not to be detected in approximately the center (KP-18) could most effectively suppress non-specific hybridization of the non-target nucleic acid with the nucleic acid probe. However, even the blocking nucleic acids whose nucleotide sequences complementary to the nucleotide not to be detected were out of approximately the center (KP-18R and KP-18l.) were shown to be capable of effectively suppressing non-specific hybridization of the non-target nucleic acid with the nucleic acid probe.

A blocking nucleic acid is shown to have been capable of effectively suppressing non-specific hybridization of the non-target nucleic acid with the nucleic acid probe even when it has one nucleotide mismatch with the nucleotide sequence of the non-target nucleic acid. In addition, all the blocking nucleic acid concentrations in the range studied in this Example enabled the effective suppression of non-specific hybridization of the non-target nucleic acid with the nucleic acid probe; however, the higher the concentration, the more effective the blockers were.

Example 3

In this Example, the length of a nucleic acid probe for detecting a target nucleic acid and the length of a blocking nucleic acid were studied.

In this example, a DNA chip on which each of the nucleic acid probes shown in Table 6 was immobilized was used.

TABLE 6

| Object To Be Detected | Probe Sequence | Length (mer) | SEQ ID NO |
|---|---|---|---|
| For Wild-type Detection | GAGCTGGTGGCGTAG | 15 | 8 |
| | TGGAGCTGGTGGCGTAGGC | 19 | 9 |
| | AGTTGGAGCTGGTGGCGTAGGCAAG | 25 | 10 |
| For Mutant Detection | GAGCTGGTGACGTAG | 15 | 11 |
| | TGGAGCTGGTGACGTAGGC | 19 | 12 |
| | AGTTGGAGCTGGTGACGTAGGCAAG | 25 | 13 |

* Underline: the sequence of codons 12 and 13, bold letter: the position of G13D mutation In this example, the genomic DNA of the strain SW948 was used as a wild-type specimen as in Example 2 and the genomic DNA of the strain LoVo was used as a mutant specimen. Using the genomic DNAs of these specimens, PCR was performed using the reaction solution shown in Table 7 below (the reaction conditions were the same as those in Table 1).

TABLE 7

| Reagent | Stock Solution Concentration | Liquid Volume (μL) |
|---|---|---|
| 10× Buffer | 10× | 5 |
| dNTP | 10 mM | 1 |
| FW | 100 μM | 0.1 |
| RV(Fluorescent Label) | 100 μM | 0.1 |
| Extracted DNA (Strain SW948, Strain LoVo) | 80 ng/μL | 0.375 |
| tap Polymerase | 5 U/μL | 0.4 |
| MilliQ | | 43.025 |
| total | | 50 |

In this example, each PCR product, a buffer solution (3×SSC/0.3% SDS/0.4 nM Cy5 oligo DNA), and 0.5 μM of a blocking nucleic acid were mixed at a ratio of 1:1:1 to make a hybridization reaction solution. The nucleotide sequence of the blocking nucleic acid used is shown in Table 8. Purified water was used as a control which contains no blocking nucleic acid.

TABLE 8

| Blocker Sequence (5'→3') | Length (mer) | SEQ ID NO |
|---|---|---|
| CTGGTGGCGT | 10 | 14 |
| GAGCTGGTGGCGTAG | 15 | 15 |
| GAGCTGGTGGCGTAGG | 16 | 16 |
| GGAGCTGGTGGCGTAGGC | 18 | 17 |
| TGGAGCTGGTGGCGTAGGC | 19 | 18 |
| AGTTGGAGCTGGTGGCGTAGGCAAG | 25 | 19 |
| GTAGTTGGAGCTGGTGGCGTAGGCAAGAGT | 30 | 20 |

* Underline: the sequence of codons 12 and 13

The resultant hybridization reaction solution was stepwise added to a DNA chip, covered with a hybridization cover, and reacted at 54° C. for 1 hour using a hybridization chamber. After the end of reaction, the solution was washed with 1×SSC/0.1% SDS for 5 minutes (vertically shaken 30 times and then allowed to stand) and with 1×SSC for 3 minutes (vertically shaken 30 times and then allowed to stand). Then, the resultant was covered with a cover film and measured for fluorescence intensity using Bioshot. And, G13D detection probe fluorescence intensity/BG (S/N ratio) was calculated based on the resultant fluorescence intensity.

Figure 5:
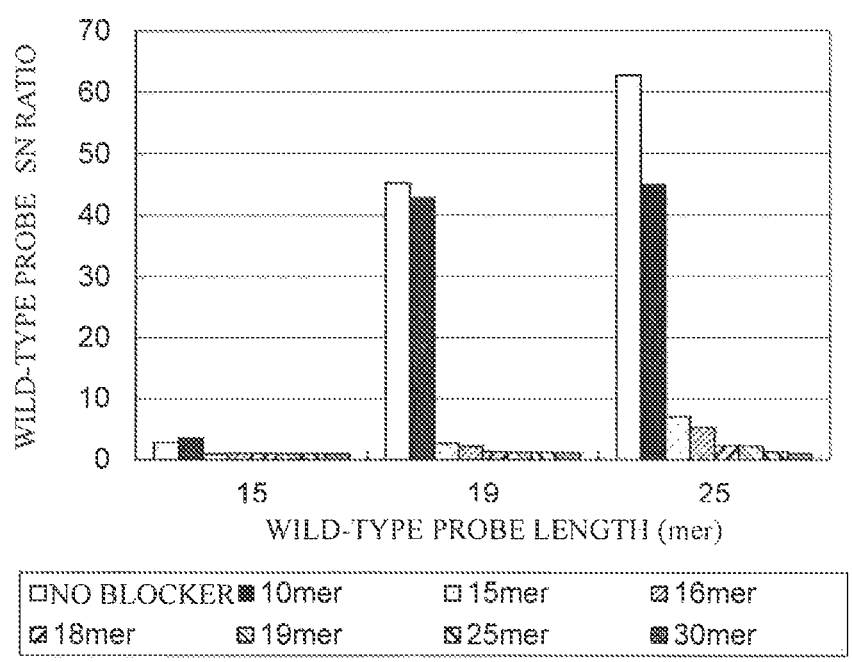
FIG. 5 is a characteristic graph showing the results of calculating G13D detection probe fluorescence intensity/BG (S/N ratio) when a wild-type specimen was used using a probe having any of various lengths and a blocking nucleic acid having any of various lengths.
Figure 6:
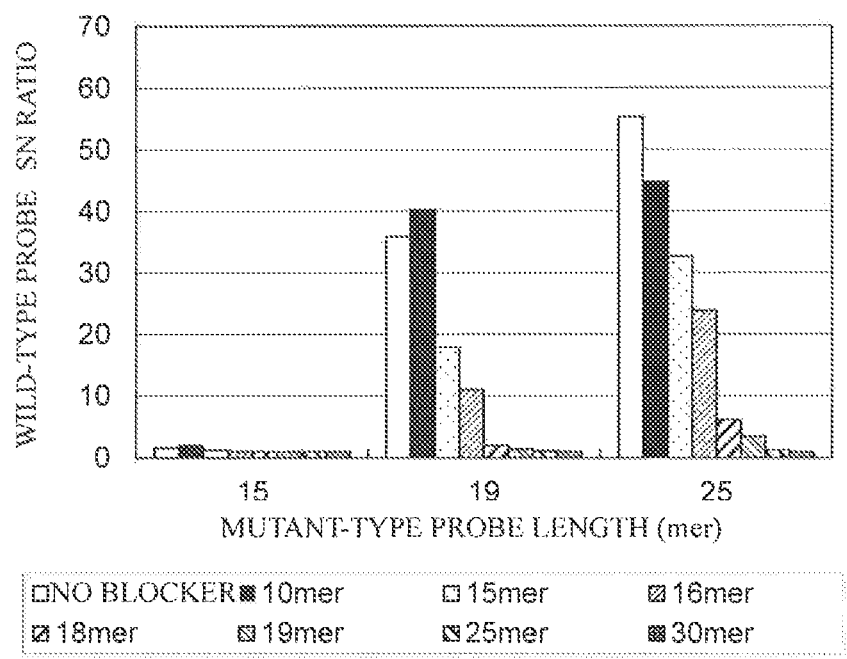
FIG. 6 is a characteristic graph showing the results of calculating G13D detection probe fluorescence intensity/BG (S/N ratio) when a mutant specimen was used using a probe having any of various lengths and a blocking nucleic acid having any of various lengths.

The results when the wild-type specimen was used are shown in FIG. 5, and the results when the mutant specimen was used are shown in FIG. 6. The results shown in FIG. 5 and the results shown in FIG. 6 were summarized in Tables 9 and 10, respectively.

TABLE 9

| Blocker | Probe Length | | |
|---|---|---|---|
| Length | 15 mer | 19 mer | 25 mer |
| None | — | — | — |
| 10 mer | x | x | x |
| 15 mer | ○ | ○ | ○ |
| 16 mer | ○ | ○ | ○ |
| 18 mer | ○ | ○ | ○ |
| 19 mer | ○ | ○ | ○ |
| 25 mer | ○ | ○ | ○ |
| 30 mer | ○ | ○ | ○ |

TABLE 10

| Blocker | Probe Length | | |
|---|---|---|---|
| Length | 15 mer | 19 mer | 25 mer |
| None | — | — | — |
| 10 mer | x | x | x |
| 15 mer | x | ○ | ○ |
| 16 mer | x | ○ | ○ |
| 18 mer | x | ○ | ○ |
| 19 mer | x | x | ○ |
| 25 mer | x | x | x |
| 30 mer | x | x | x |

As shown in FIG. 5, the blocking nucleic acid length of 10 mers resulted in the SN ratio roughly comparable to that when the blocking nucleic acid was not contained and did not enable the suppression of non-specific hybridization of the non-target nucleic acid with the nucleic acid probe. FIG. 5 also showed that the blocking nucleic acid length of 15 mers or more enabled the suppression of non-specific hybridization of the non-target nucleic acid with the nucleic acid probe. From these results, it was probable that the blocking nucleic acid length was preferably 60% or more of the nucleic acid probe length (when the blocking nucleic acid was 15 mers in length, 15 mers (blocking nucleic acid)/25 mers (nucleic acid probe)=60%)

FIG. 6 showed that when the length of the blocking nucleic acid was the same length of the nucleic acid probe, the SN ratio was significantly decreased for a mutant specimen having one nucleotide mismatch, resulting in the disappearance of specificity. From the above results, it was probably recommended that the length of the blocking nucleic acid be 60% (inclusive) to 100% (exclusive) of the nucleic acid probe length.

All publications, patents, and patent applications cited in this application are intended to be incorporated herein by reference in their entirety.

The invention claimed is:

1. A method for detecting a target nucleic acid by hybridization of the target nucleic acid comprising a nucleotide to be detected with a nucleic acid probe, wherein the nucleic acid probe comprises a nucleotide sequence complementary to the target nucleic acid, the method comprising:
   (a) amplifying the target nucleic acid to obtain a reaction solution;
   (b) mixing a buffer composition for hybridization with the reaction solution comprising the target nucleic acid, wherein the buffer composition for hybridization comprises a blocking nucleic acid comprising a nucleotide sequence complementary to a non-target nucleic acid and having a length of 60% or more and less than 100% of the nucleotide length of the nucleic acid probe, wherein the non-target nucleic acid comprises a nucleotide not to be detected corresponding to the nucleotide to be detected;
   (c) hybridizing the nucleic acid probe with the target nucleic acid, wherein the target nucleic acid and the non-target nucleic acid have identical nucleic acid sequences except for the nucleotide to be detected; and then
   (d) detecting the target nucleic acid using the nucleic acid probe.

2. The method according to claim 1, wherein the nucleic acid probe is 15 to 25 bases in length and the blocking nucleic acid is 15 to 24 bases in length.

3. The method according to claim 1, wherein a mixed solution of the buffer composition for hybridization and the reaction solution comprising the target nucleic acid is contacted with a microarray in which the nucleic acid probe is immobilized on a substrate.

4. The method according to claim 1, wherein the buffer composition for hybridization further comprises sodium citrate dihydrate (SSC) and sodium dodecyl sulfate (SDS).

5. The method according to claim 1, wherein the reaction solution comprising the target nucleic acid is a reaction solution after nucleic acid amplification reaction for amplifying the target nucleic acid and the reaction solution is mixed with the buffer composition for hybridization.

* * * * *